US00PP27778P3

(12) United States Plant Patent
Gmitter, Jr.

(10) Patent No.: US PP27,778 P3
(45) Date of Patent: Mar. 14, 2017

(54) MANDARIN TREE NAMED 'BINGO'

(50) Latin Name: ***Citrus reticulata* hybrid×*Citrus kinokuni* 'Mukakukishu'**
Varietal Denomination: Bingo

(71) Applicant: Florida Foundation Seed Producers, Inc., Marianna, FL (US)

(72) Inventor: Frederick G. Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 57 days.

(21) Appl. No.: 14/544,780

(22) Filed: Feb. 12, 2015

(65) Prior Publication Data

US 2016/0242334 P1 Aug. 18, 2016

(51) Int. Cl.
*A01H 5/08* (2006.01)

(52) U.S. Cl.
USPC ..... Plt./202

(58) Field of Classification Search
USPC ..... Plt./156, 201, 202
See application file for complete search history.

(56) References Cited

U.S. PATENT DOCUMENTS

PP21,356 P3 10/2010 Gmitter, Jr. et al.
2015/0047083 P1 2/2015 Grosser

*Primary Examiner* — Susan McCormick Ewoldt
*Assistant Examiner* — Karen Redden
(74) *Attorney, Agent, or Firm* — Dentons US LLP

(57) ABSTRACT

The new mandarin tree called 'Bingo' arose from a seedling tree selected among a family of hybrids from a cross of the seed parent LB7-11 and pollen parent 'Seedless Kishu'. The new tree produces annual crops of well-colored fruit that are essentially seedless, very easy to peel, mature early in the season, and are of excellent eating quality.

5 Drawing Sheets

Latin name of the genus and species of the plant claimed: *Citrus reticulata* hybrid×*Citrus kinokuni* 'Mukakukishu'.

Variety denomination: 'Bingo'.

BACKGROUND OF THE INVENTION

The present invention relates to a new and distinct early maturing, seedless, and convenient-to-consume mandarin hybrid called 'Bingo'. This cultivar arose from a seedling tree selected among a family of hybrids from a cross of the seed parent LB7-11 (an unnamed, unreleased breeding line, itself a hybrid of 'Clementine' mandarin crossed with 'Valencia' sweet orange) and pollen parent 'Seedless Kishu' (known as 'Mukakukishu' in Japan), an unpatented, small-fruited mandarin cultivar. The cross was made in Lake Alfred, Fla. in spring 2005, and the original seedling tree was planted in the field in Lake Alfred, Fla. spring 2007. The cultivar was first selected in autumn 2013, when its distinctive appearance and unique qualities were first noted, including the significantly greater-than-average health of the tree itself, which has demonstrated substantial field tolerance to Huanglongbing disease (HLB or citrus greening). 'Bingo' was first asexually propagated in October 2014 by topworking onto a citrus rootstock in Vero Beach, Fla. The claimed tree reproduces true to type and is stable in successive generations.

The original parent tree 'LB7-11' no longer exists. However, it differed from claimed variety 'Bingo' in several aspects. 'LB7-11' matured in mid-November to early December, while 'Bingo' matures from late September to early November. 'LB7-11' also had a thicker rind and was more difficult to peel than 'Bingo'. 'LB7-11' regularly had 10-20 monoembryonic seeds per fruit under cross pollination, while 'Bingo' is completely seedless, even under intensive cross-pollination conditions.

'Seedless Kishu' matures at a similar time as 'Bingo' in Florida, although generally tends to be slightly later. The fruit of 'Bingo' are larger, more intensely pigmented externally and internally, and they hold on the tree longer and have a substantially longer post-harvest period than 'Seedless Kishu'. 'Bingo' flowers are also larger than those of 'Seedless Kishu'.

'Fanglo' and 'US Early Pride' (U.S. Plant Pat. No. 23,724, a mutant selected from irradiated 'Fanglo') may be harvested in Florida at the same season. 'Fanglo' has numerous seeds, and 'US Early Pride' is lower in seed number, while 'Bingo' is always seedless. 'Bingo' produces a smaller fruit, which peels much easier and cleaner than 'Fanglo' and 'US Early Pride'.

'Clementine' mandarins are harvested in California at nearly the same season, and marketed throughout the US. 'Bingo' differs by its much deeper orange-red color internally and externally. 'Bingo' is easier to peel, and has much higher Brix, and in general better eating quality. Further, if cross pollinated, 'Clementine' fruit also will produce seeds.

Fruit of 'Bingo' were harvested Sep. 30, 2015 and some were exposed to ethylene (4.5-5.0 ppm) for 48 hours, 29° C., 95% relative humidity and then stored at 4° C. for up to 8 weeks. 'Fanglo', the common Florida mandarin cultivar harvested in the same season, was exposed to the same conditions, with the exception that the ethylene exposure time was 24 hours. After 6 weeks of storage, fruit of both cultivars, treated and untreated, were 100% healthy. After 8 weeks in storage, 92.3% of treated 'Bingo' fruit and 92.85% and untreated 'Bingo' fruit remained healthy. By contrast, 67% of treated fruit of 'Fanglo' and 83% untreated fruit of 'Fanglo' remained healthy.

SUMMARY OF THE INVENTION

The following detailed description sets forth the distinctive characteristics of 'Bingo'. This cultivar produces annual crops of well-colored fruit that are essentially seedless, very easy to peel, mature early in the season, and are of excellent eating quality. The present botanical description is that of the variety grown as a 7-8 year-old tree growing on its own roots in Lake Alfred, Fla. The colors (except those in common terms) are described using The R.H.S. Colour Chart published by The Royal Horticultural Society in London (second edition), in association with the Flower Council of Holland.

BRIEF DESCRIPTION OF THE DRAWINGS

This new mandarin hybrid tree is illustrated by the accompanying photographs which show the tree's form, foliage, and fruit. The colors shown are as true as can be reasonably obtained by conventional photographic procedures. The photographs and phenotypic description provided herein are of a tree approximately 8-years old.

FIG. 1—Shows the overall mature plant growth habit in the fall time.

FIG. 2—Shows mature fruits hanging on the tree; fruit and foliage in upper right corner of photo is from an adjacent tree, from a different hybrid.

FIG. 3—Shows a close-up of leaves and mature fruits.

FIG. 4—Shows a close-up of the mature fruit.

FIG. 5—Shows a close-up of the mature fruit with the rind and cross-sectional view of the fruit when cut in the center.

DETAILED BOTANICAL DESCRIPTION

Phenotypic Description of 'Bingo'

Figure 1:
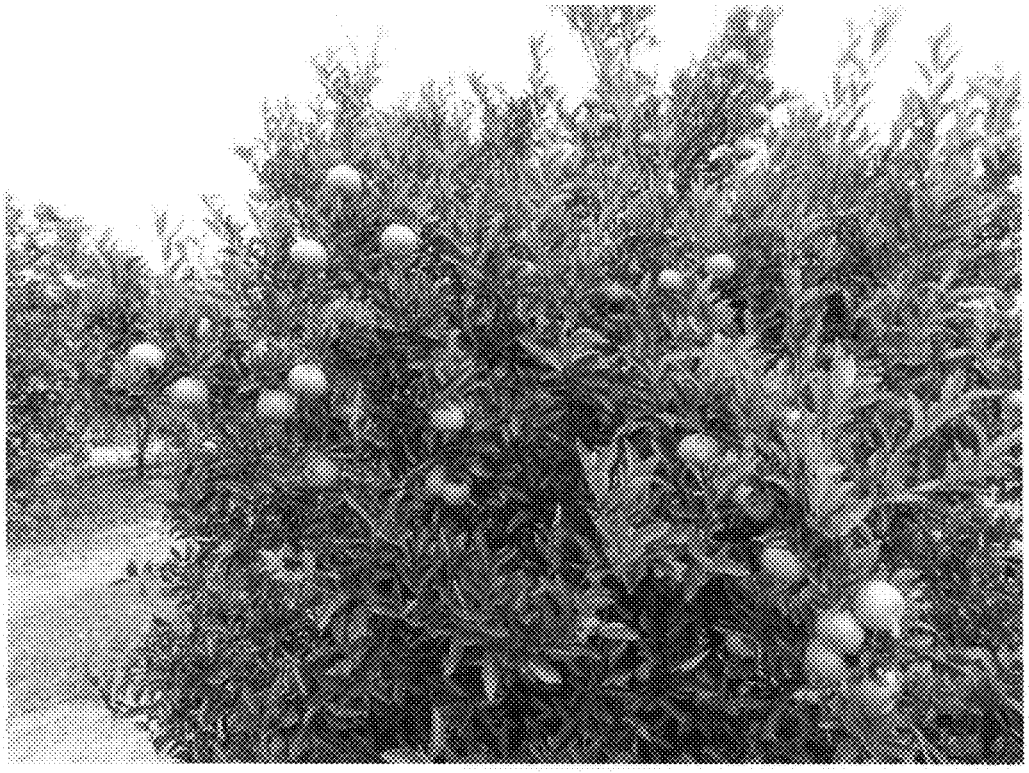
FIGS. 1-3 were taken in the fall.
Figure 2:
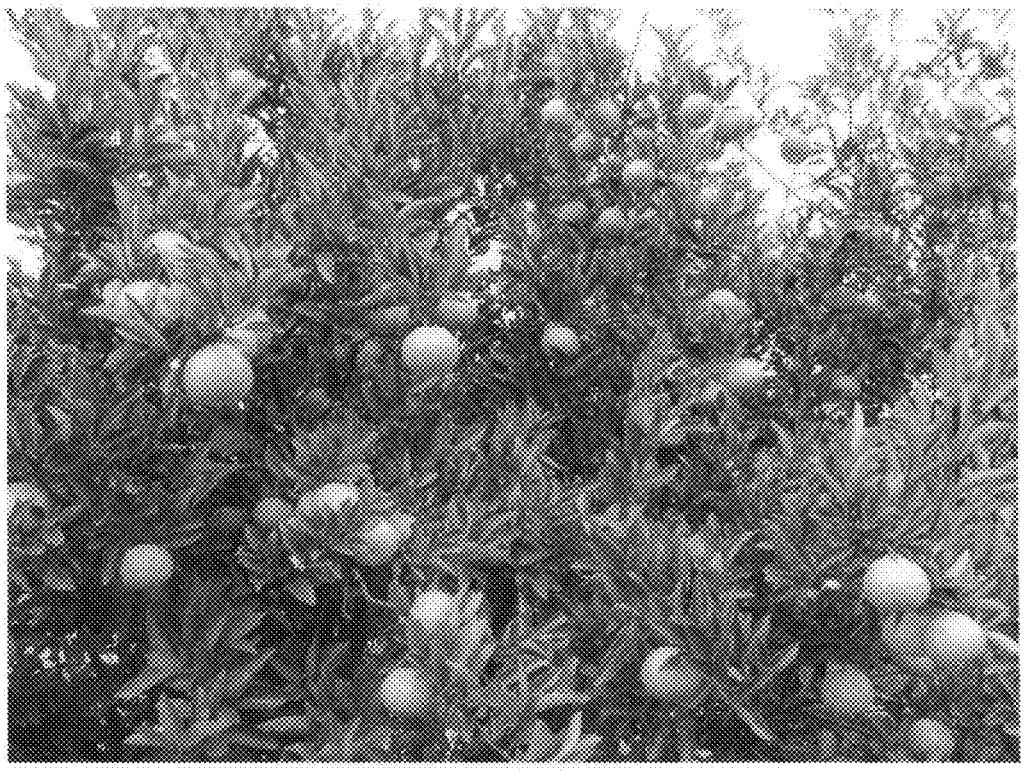
Figure 3:
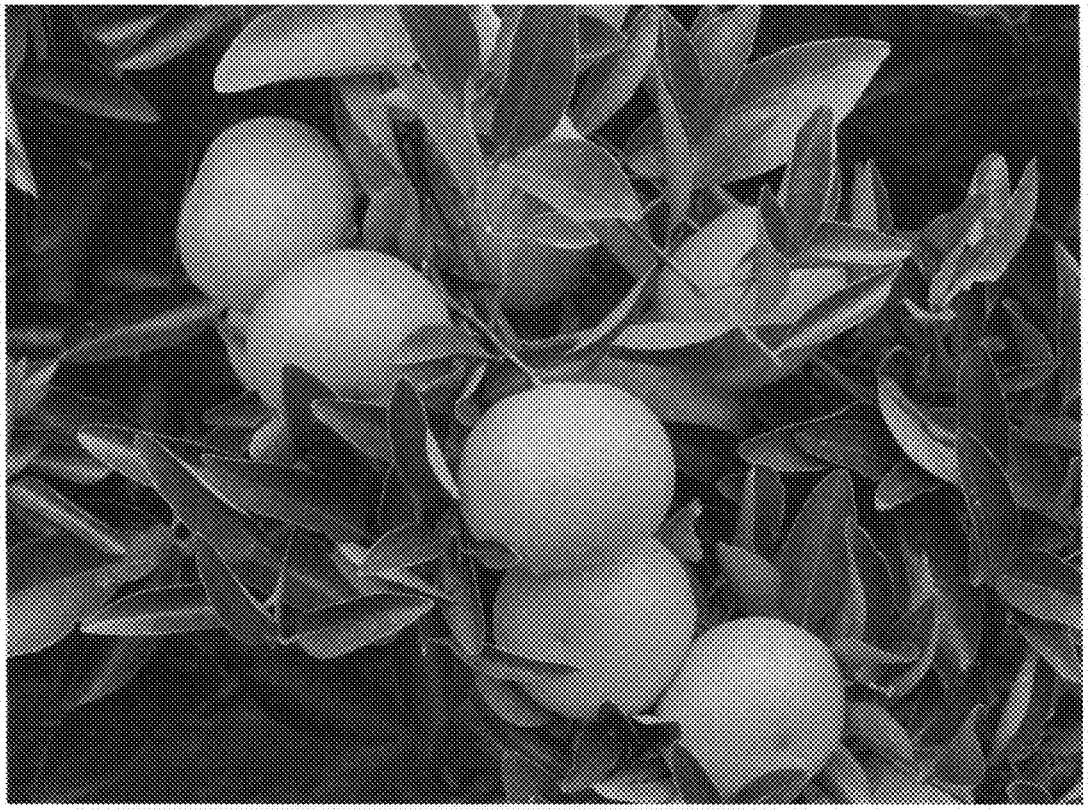
Figure 4:
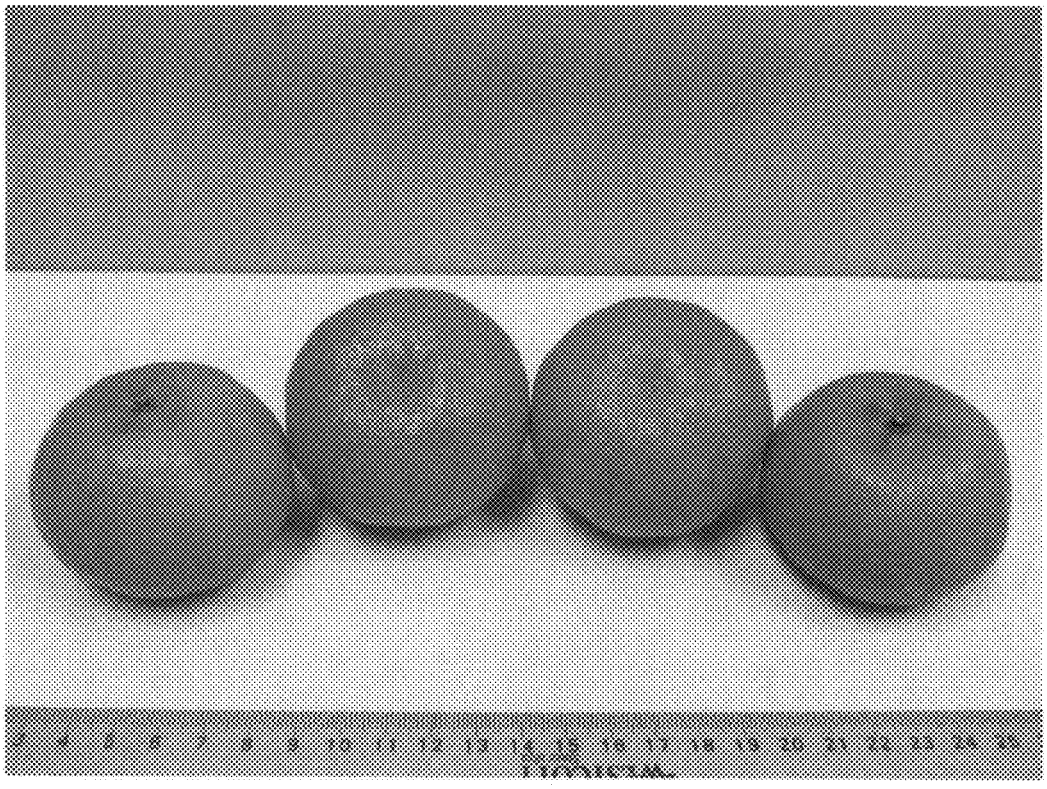
FIGS. 4-5 were taken during the early winter from the same tree.
Figure 5:
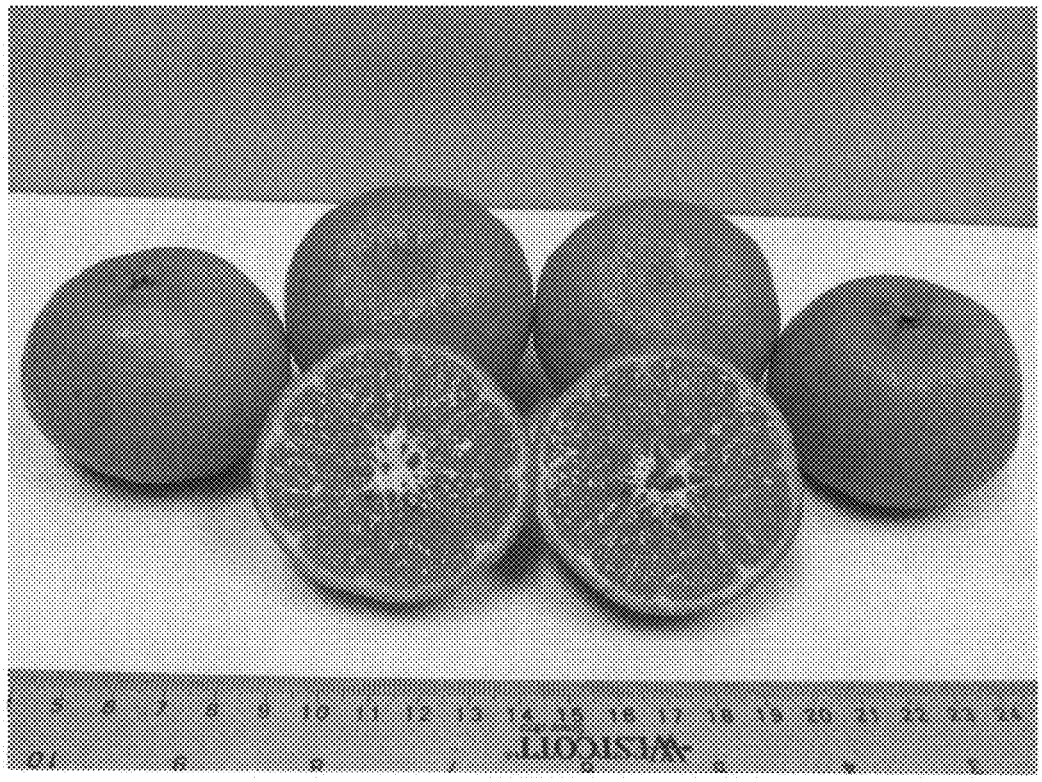

Classification:

*Botanical.*—*Citrus reticulata* hybrid×*Citrus kinokuni* 'Mukakukishu'.

*Common name.*—Mandarin hybrid or Tangerine.

Parentage:

*Female parent.*—LB7-11, an unpatented, unreleased hybrid of 'Clementine' mandarin×'Valencia' sweet orange.

*Male parent.*—'Seedless Kishu' (unpatented; also known as 'Mukakukishu').

Tree:

*Ploidy.*—Diploid.

*Size.*—Small to Medium.

*Height.*—2.7 m.

*Tree spread.*—1.8 to 2.2 m.

*Vigor.*—Vigorous.

*Density.*—Canopy is quite dense.

*Form.*—The tree has an obloid shape with lateral and upright branches growing. Branches with fruit exhibit drooping.

*Growth habit.*—Both upright and lateral growth, with more lateral growth.

Trunk:

*Trunk diameter.*—8.7 cm in diameter at a height of 30 cm above the ground, 7 year old tree.

*Trunk texture.*—Smooth.

*Trunk bark color.*—RHS 197A (greyed-green); irregularly striated with RHS 137B (green).

Branches:

*Crotch angle.*—First crotch forms a 25- to 30-degree angle, middle crotch forms a 35-degree angle.

*Branch length.*—Branch reaches 1.8 m from the first crotch to the tip of the branch.

*Branch texture.*—Relatively smooth, occasionally with small thorns or spines.

*Branch color* (*shoots from previous flush, hardened and 4 to 5 mm in diameter*).—RHS 138A (green).

Leaves:

*Size* (*lamina average*).—Length: 103.5 mm. Width: 52 mm. L/W ratio: 1.99.

*Thickness.*—Regular and average compared to commercial mandarin hybrids.

*Type.*—Simple.

*Arrangement.*—Alternate.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS N137A (green). Lower surface (abaxial): RHS 146A (yellow-green).

*Petiole.*—Shape: Brevipetiolate (shorter than leaf lamina); junction between petiole and lamina is articulate. Width (petiole wing): Very narrow. Shape (petiole wing): Obovate. Length: 10.9 to 11.1 mm. Width: 2.0 to 2.3 mm. Color: RHS N137A (green).

Flowers and flower buds:

*Type.*—Hermaphrodite.

*Bearing.*—Flowers grow from leaf axillaries and leaf terminals singly and in small clusters, single flower and double flowers growing from leaf axillaries have been seen. Each flower branch consists of 7-10 flowers.

*Flower diameter.*—Fully open flower has an average diameter of 16.5 to 19 mm.

*Flower depth.*—Typical flower has an average depth of 10.3 to 10.6 mm.

*Flower blooming period.*—First bloom: Observed Mar. 1, 2014. Full bloom: Observed Mar. 12, 2014.

*Flower bud size.*—Length: Initial visible flower bud is 2.3 mm in length; mature flower bud is 9.4 mm in length. Diameter: Initial visible flower bud is 2.5 mm in diameter; mature flower bud is 4.9 mm in diameter. Shape: Initial visible flower bud has round ball shape; mature flower bud has elongated olive shape. Color: RHS 144B (yellow-green) for initial visible flower bud; RHSNN155C (white) for mature flower bud with RHS 150D (yellow-green) spots distributed at tip of the flower bud.

*Flower petals.*—Shape: Flat, spatula shaped. Apex shape: Smooth, acute shaped. Base shape: Even obtuse.

*Color.*—Upper surface: RHS NN155C (white). Lower surface: RHS NN155C (white) with RHS 150D (yellow-green) spots distributed toward to the petal apex. Margin: Smooth.

*Sepal*.—Number: 5 per flower. Shape: Delta shaped with acute angle at apex. Length: 1.4 mm. Width: 2.1 mm. Apex shape: Triangle shaped. Margin: Smooth.

*Color*.—Upper surface: RHS 149D yellow-green). Lower surface: RHS 149C (yellow-green).

*Fragrance*.—Moderately fragrant.

*Pedicel*.—Length: 5.2 to 5.4 mm. Diameter: 0.7 to 0.8 mm. Color: RHS 143C (green).

*Reproductive organs*.—Fertility: Appears self-fertile. Stamen length: 5.0 to 5.2 mm. Anther length: 1.1 mm. Anther width: 0.5 to 0.6 mm. Anther color: RHS 18A (yellow-orange). Anther filament length: 3.7 to 3.8 mm. Pollen amount: Moderate. Pollen color (general): RHS 14A (yellow-orange). Pistil number: 1. Pistil length: 5.7 to 6.0 mm. Pistil color: RHS 12B (yellow). Style length: 4.6 mm. Style diameter: 0.8 to 0.9 mm. Style color: RHS 150C (yellow-green). Ovary shape: Oval shaped. Ovary: diameter: 1.9 mm. Ovary color: RHS 145A (yellow-green).

Fruit:

*Size*.—Uniform.

*Tall*.—49.5 to 51.4 mm on average.

*Width*.—59.7 to 62.5 mm on average.

*Average weight* (*per individual fruit*).—93.2 g.

*Shape*.—Round.

*Shape* (*cross-section*).—Round.

*Apex*.—Truncated with shallow dent.

*Apex cavity diameter*.—N/A.

*Base*.—Short neck or no neck with wrinkle.

*Base cavity diameter*.—5.7 to 6.1 mm.

*Harvesting*.—First pick around Oct. 15, 2014 (based on season and rootstock); last pick around Dec. 15, 2014, although fruit continue to hold on the tree for a longer time (based on season and rootstock).

*Fruit stem* (*short stem connecting the fruit*).—Length: 5.4 mm. Diameter: 2.5 mm. Color: RHS 199B (greyed-brown) with RHS 138A (green) strip.

*Productivity*.—The crop is substantial on an annual basis. No quantitative measure is available to date. Performance of the cultivar (increased fruit size) can be enhanced by deliberate fruit thinning earlier in the season.

Skin:

*Adherence*.—Adherence between albedo (mesocarp) and flesh (endocarp) is very loose, very easy to peel. The adherence is evenly distributed from base to apex.

*Thickness*.—2.3 to 2.4 mm on average.

*Texture*.—Smooth.

*Color*.—Flavedo (epicarp): Ranges between RHS N25B (orange) to RHS N25A (orange). Albedo (mesocarp): RHS 23A (yellow-orange).

*Stylar end*.—Closed.

*Rind oil cell density*.—224 oil cells/square cm.

Flesh:

*Number of segments*.—Average between 10 and 11 segments per fruit.

*Segment walls*.—Medium soft with sufficient strength to maintain integrity as separated.

*Juice*.—Abundant.

*Color*.—Uniformly RHS 25A (orange).

*Texture*.—Firm to medium soft.

*Vesicles*.—Length: arranged from 11.5 to 11.8 mm on average. Diameter (thickness): 3.2 to 3.4 mm on average.

*Eating quality*.—Soluble solids (average): 11.6 Brix on Oct. 20, 2014; 12.5 Brix on Nov. 9, 2014.

*Acidity* (*average*).—0.81% on Oct. 20, 2014; 0.83 on Nov. 9, 2014.

*Ratio*.—14.32 on Oct. 20, 2014; 15.06 on Nov. 9, 2014.

Seeds: Seedless, although small but insignificant seed traces can be found.

Resistance to disease: The cultivar has demonstrated substantial field tolerance of HLB; the block in which the hybrid was grown and selected has been severely and uniformly challenged by this disease, with nearly all trees symptomatic, severely declining, or already dead. To date, the causal agent for HLB, *Candidatus Liberibacter asiaticus*, has not been detected using the most sensitive qPCR detection methodology. No rigorous systematic disease resistance testing has been conducted, but the following observations have been made in the field. In addition to severe HLB pressure in the field plot where the original tree was grown, several other citrus diseases common in Florida are endemic in the orchard, including citrus canker (*Xanthomonas citri* subsp. citri (synonym: *X. axonopodis* pv. citri)), Alternaria brown spot (*Alternaria alternata*), and citrus scab (*Elsinoë fawcettii*). None of these diseases have been observed on either foliage or fruit over 2.5 years of careful observation.

What is claimed is:

1. A new and distinct mandarin tree called 'Bingo' as illustrated and described herein.

* * * * *